United States Patent [19]

Sarges

[11] 4,235,911
[45] Nov. 25, 1980

[54] HYDANTOIN DERIVATIVES

[75] Inventor: Reinhard Sarges, Mystic, Conn.

[73] Assignee: Pfizer Inc., New York, N.Y.

[21] Appl. No.: 48,004

[22] Filed: Jun. 13, 1979

[51] Int. Cl.³ .................... C07D 471/10; A61K 31/47
[52] U.S. Cl. ...................................... 424/258; 546/18; 424/256
[58] Field of Search .................. 546/18; 424/256, 258

[56]   References Cited
U.S. PATENT DOCUMENTS
3,821,383   6/1974   Sestanj et al. .......................... 424/258

OTHER PUBLICATIONS

Faust, et al., J. American Pharm. Assoc., 46, (1957), pp. 118-124.

Primary Examiner—Joseph Paul Brust

Attorney, Agent, or Firm—Connolly and Hutz

[57] ABSTRACT

A series of novel tetrahydroquinoline-derived spirohydantoin compounds has been prepared, including their pharmaceutically acceptable acid addition salts. These particular compounds are useful in therapy as aldose reductase inhibitors for the control of certain chronic diabetic complications. Preferred member compounds include 1'-methyl-1',2',3',4'-tetrahydro- spiro-[imidazolidine-4,4'-quinoline]-2,5-dione, 6'-chloro-1',2',3',4'-tetrahydro-spiro-[imidazolidine-4,4'-quinoline]-2,5-dione, 7'-chloro-1',2',3',4'-tetrahydro-spiro-[imidazolidine-4,4'-quinoline]-2,5-dione and 1'-methyl-1',2',3',4'-tetrahydro-spiro-[imidazolidine-4,4'-pyrido(2,3-b)pyridine]-2,5-dione. Methods for preparing these compounds from known starting materials are provided.

8 Claims, No Drawings

HYDANTOIN DERIVATIVES

BACKGROUND OF THE INVENTION

This invention relates to new and useful hydantoin derivatives of principal interest to those in the field of medicinal chemistry and/or chemotherapy. More particularly, it is concerned with a novel series of tetrahydroquinoline-derived spiro-hydantoin compounds, which are of especial value in view of their ability to effectively control certain chronic complications arising from diabetes mellitus (e.g., diabetic cataracts, retinopathy and neuropathy). The invention also includes a new method of therapy within its scope.

In the past, various attempts have been made by numerous investigators in the field of organic medicinal chemistry to obtain new and better oral antidiabetic agents. For the most part, these efforts have involved the synthesis and testing of various heretofore new and unavailable organic compounds, particularly in the area of the sulfonylureas, in an endeavor to determine their ability to lower blood sugar (i.e., glucose) levels to a substantially high degree when given by the oral route of administration. However, in the search for newer and still more effective antidiabetic agents, little is known about the effect of other organic compounds in preventing or arresting certain chronic complications of diabetes, such as diabetic cataracts, neuropathy and retinopathy, etc. Nevertheless, K. Sestanj et al. in U.S. Pat. No. 3,821,383 do disclose that certain aldose reductase inhibitors like 1,3-dioxo-1H-benz[d,e]-isoquinoline-2(3H)-acetic acid and some closely-related derivatives thereof are useful for these purposes even though these particular compounds are not known to be hypoglycemic per se. These particular aldose reductase inhibitors all function by inhibiting the activity of the enzyme aldose reductase, which is primarily responsible for catalyzing the reduction of aldoses (like glucose and galactose) to the corresponding polyols (such as sorbitol and galactitol) in the human body. In this way, unwanted accumulations of galactitol in the lens of galactosemic subjects and of sorbitol in the lens, retina, peripheral nervous system and kidney of various diabetic subjects are thereby prevented or otherwise reduced as the case may be. As a result, these compounds are definitely of value as aldose reductase inhibitors for controlling certain chronic diabetic complications, including those of an ocular nature, since it is already known in the art that the presence of polyols in the lens of the eye quite often leads to cataract formation together with a concomitant loss of lens clarity.

SUMMARY OF THE INVENTION

In accordance with the present invention, it has now been rather surprisingly found that various novel tetrahydroquinoline spiro-hydantoin compounds are extremely useful when employed in therapy as aldose reductase inhibitors for the control of certain chronic complications arising in a diabetic subject. More specifically, the novel compounds of this invention are all selected from the group consisting of tetrahydroquinoline-derived spiro-hydantoin bases of the formulae:

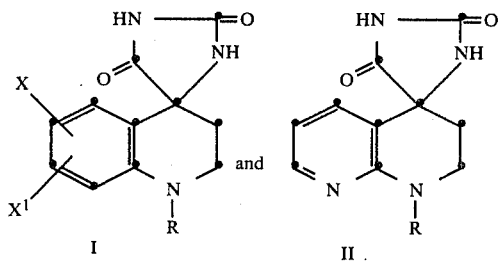

and the pharmaceutically acceptable acid addition salts thereof, wherein X is hydrogen and $X^1$ is hydrogen, lower alkoxy, fluorine, chlorine, bromine or phenyl; X and $X^1$, when taken separately, are each lower alkoxy, chlorine or phenyl, and when taken together are $-OCH_2(CH_2)_nO-$ wherein n is zero or one, and R is hydrogen or lower alkyl, with the proviso that R is always other than hydrogen when $X^1$ is hydrogen. These novel compounds are all potent aldose reductase inhibitors and, therefore, possess the ability to markedly reduce or even inhibit sorbitol accumulation in the lens and peripheral nerves of various diabetic subjects.

Of especial interest in this connection are such typical and preferred member compounds of the invention as 1'-methyl-1',2',3',4'-tetrahydro-spiro-[imidazolidine-4,4'-quinoline]-2,5-dione, 6'-chloro-1',2',3',4'-tetrahydro-sprio-[imidazolidine-4,4'-quinoline]-2,5-dione, 7'-chloro-1',2',3',4'-tetrahydro-spiro-[imidazolidine-4,4'-quinoline]-2,5-dione and 1'-methyl-1',2',3',4'-tetrahydro-spiro-[imidazolidine-4,4'-pyrido(2,3-b)pyridine]-2,5-dione, respectively. These particular compounds are all highly potent as regards their aldose reductase inhibitory activity, in addition to being extremely effective in lowering sorbitol levels in the lens and sciatic nerve of diabetic subjects and galactitol levels in the lens of galactosemic subjects to a rather substantially high degree.

DETAILED DESCRIPTION OF THE INVENTION

In accordance with the process employed for preparing the novel compounds of this inventon (viz., those of structural formulae I-II), an appropriate carbonyl ring compound, such as the corresponding 2,3-dihydro-4(1H)-quinolone or 2,3-dihydro-4(1H)-pyrido(2,3-b)pyridone, of the respective formulae:

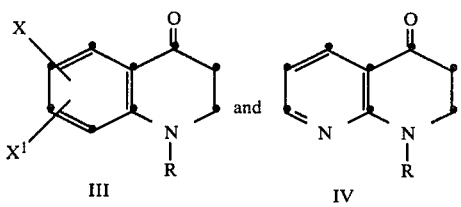

wherein X, $X^1$ and R are each as previously defined (with proviso), is condensed with an alkali metal cyanide (e.g. sodium cyanide or potassium cyanide) and ammonium carbonate to form the desired tetrahydroquinoline-derived spiro-hydantoin final product of the structural formulae previously indicated. This particular reaction is normally carried out in the presence of a reaction-inert polar organic solvent medium in which both the reactants and reagents are mutually miscible. Preferred organic solvents for use in this connection include cyclic ethers such as dioxane and tetrahydrofuran, lower alkylene glycols like ethylene glycol and trimethylene glycol, water-miscible lower alkanols such as methanol, ethanol and isopropanol, as well as N,N-di(lower alkyl) lower alkanoamides like N,N-dimethylformamide, N,N-diethylformamide and N,N-dimethylacetamide etc. In general, the reaction is conducted at a temperature that is in the range of from about 50° C. up to about 150° C. for a period of about two hours to about four days. Although the amount of reactant and reagents employed in the reaction can vary to some extent, it is preferable to employ at least a slight molar excess of the alkali metal cyanide reagent with respect to the carbonyl ring compound starting material in order to effect maximum yield. Upon completion of the reaction, the desired product is easily isolated in a conventional manner, e.g., by first diluting the reaction mixture with water (boiling if necessary) and then cooling the resultant aqueous solution to room temperature, followed by acidification to afford the particular tetrahydroquinoline-derived spiro-hydantoin compound in the form of a readily-recoverable salt.

The starting materials required for preparing the spiro-hydantoin compounds of this invention are, for the most part, known compounds or else they can easily be synthesized by those skilled in the art starting from more readily available materials according to conventional methods of organic chemistry. For instance, 2,3-dihydro-1-methyl-4(1H)-quinolone (a compound of structural formula III) is a known compound which is prepared according to the general procedure described in the *Journal of Medicinal Chemistry*, Vol. 8, p. 566 (1965), while 2,3-dihydro-4(1H)-pyrido(2,3-b)pyridone (a known compound of structural formula IV) is prepared according to an analogous procedure set forth in the *Journal of Medicinal Chemistry*, Vol. 18, p. 1038 (1975). On the other hand, 6-chloro-2,3-dihydro-4(1H)-quinolone and 7-chloro-2,3-dihydro-4(1H)-quinolone (both known compounds of structural formula III) are each individually prepared according to the general procedures originally disclosed in the *Journal of Organic Chemistry*, Vol. 28, p. 1135 (1963).

The pharmaceutically acceptable acid addition salts of the tetrahydroquinoline-derived spiro-hydantoin base compounds of this invention are prepared by simply treating the aforementioned organic bases with various mineral and organic acids which form non-toxic acid addition salts having pharmacologically acceptable anions, such as the hydrochloride, hydrobromide, hydroiodide, sulfate or bisulfate, phosphate or acid phosphate, acetate, lactate, maleate, fumarate, citrate or acid citrate, tartrate or bitartrate, succinate, gluconate, saccharate, methanesulfonate, ethanesulfonate, benzenesulfonate and p-toluenesulfonate salts. For instance, the salt-formation step may be carried out by using a substantially equimolar amount of the appropriate acid in an aqueous solvent medium or in a suitable organic solvent such as methanol or ethanol. Upon careful evaporation of the solvent, the solid salt is readily obtained.

As previously indicated, the tetrahydroquinoline-derived spiro-hydantoin compounds of this invention are all readily adapted to therapeutic use as aldose reductase inhibitors for the control of chronic diabetic complications, in view of their ability to reduce lens sorbitol levels in diabetic subjects to a statistically significant degree. For instance, 6'-chloro-1',2',3',4'-tetrahydro-spiro-[imidazolidine-4,4'-quinoline]-2,5-dione, a typical and preferred agent of the present invention, has been found to consistently control (i.e., inhibit) the formation of sorbitol levels in diabetic rats to a significantly high degree when given by the oral route of administration at dose levels ranging from 5.0 mg./kg. to 25 mg./kg., respectively, without showing any substantial signs of toxic side effects. The other compounds of this invention also cause similar results. Furthermore, all the herein described compounds of this invention can be administered by either the oral or parenteral routes of administration, for the present purposes at hand, without causing any significant untoward pharmacological side reactions to occur in the subject to whom they are so administered. In general, these compounds are ordinarily administered in dosages ranging from about 0.25 mg. to about 25 mg. per kg. of body weight per day, although variations will necessarily occur depending upon the weight and condition of the subject being treated and the particular route of administration chosen.

In connection with the use of the tetrahydroquinoline-derived spiro-hydantoin compounds of this invention for the treatment of diabetic subjects, it is to be noted that these compounds may be administered either alone or in combination with pharmaceutically acceptable carriers by either of the routes previously indicated, and that such administration can be carried out in both single and multiple dosages. More particularly, the compounds of this invention can be administered in a wide variety of different dosage forms, i.e., they may be combined with various pharmaceutically-acceptable inert carriers in the form of tablets, capsules, lozenges, troches, hard candies, powders, sprays, aqueous suspensions, injectable solutions, elixirs, syrups, and the like. Such carriers include solid diluents or fillers, sterile aqueous media and various non-toxic organic solvents, etc. Moreover, such oral pharmaceutical formulations can be suitably sweetened and/or flavored by means of various agents of the type commonly employed for just such purposes. In general, the therapeutically useful compounds of this invention are present in such dosage forms at concentration levels ranging from about 0.5% to about 90% by weight of the total composition, i.e., in amounts which are sufficient to provide the desired unit dosage.

For purposes of oral administration, tablets containing various excipients such as sodium citrate, calcium carbonate and calcium phosphate may be employed along with various disintegrants such as starch and preferably potato or tapioca starch, alginic acid and certain complex silicates, together with binding agents such as polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include the high molecular weight polyethylene glycols. When aqueous suspensions and/or elixirs are desired for oral administration, the essential active ingredient therein may be combined with various sweetening or flavoring agents, coloring matter or dyes, and if so desired, emulsifying and/or suspending agents as well, together with such diluents as water, ethanol, propylene glycol, glycerin and various like combinations thereof.

For purposes of parenteral administration, solutions of these particular tetrahydroquinoline-derived spirohydantoins in sesame or peanut oil or in aqueous propylene glycol or N,N-dimethylformamide may be employed, as well as sterile aqueous solutions of the corresponding water-soluble, non-toxic mineral and organic acid addition salts previously enumerated. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal injection purposes. In this connection, the sterile aqueous media employed are all readily obtainable by standard techniques well-known to those skilled in the art. Additionally, it is also possible to administer the aforesaid spirohydantoin compounds topically via an appropriate opthalmic solution suitable for the present purposes at hand, which can then be given dropwise to the eye.

The activity of the compounds of the present invention, as agents for the control of chronic diabetic complications, is determined by their ability to successfully pass one or more of the following standard biological and/or pharmacological tests, viz., (1) measuring their ability to inhibit the enzyme activity of isolated aldose reductase; (2) measuring their ability to reduce or inhibit sorbitol accumulation in the sciatic nerve of acutely streptozotocinized (i.e., diabetic) rats; (3) measuring their ability to reverse already-elevated sorbitol levels in the sciatic nerve and lens of chronic streptozotocin-induced diabetic rats; (4) measuring their ability to prevent or inhibit galactitol formation in the lens of acutely galactosemic rats, and (5) measuring their ability to delay cataract formation and reduce the severity of lens opacities in chronic galactosemic rats.

EXAMPLE 1

A mixture consisting of 1.61 g. (0.01 mole) of 2,3-dihydro-1-methyl-4(1H)-quinolone [prepared according to the procedure described in the *Journal of Medicinal Chemistry*, Vol. 8, p. 566 (1965)], 0.78 g. (0.012 mole) of potassium cyanide and 5.09 g. (0.053 mole) of powdered ammonium carbonate in 40 ml. of denatured ethanol was heated in an oil bath at 65° C. for a period of 17 hours. The reaction mixture was then poured into 300 ml. of water and the pH subsequently adjusted to a value of 8.0 with the aid of 6 N hydrochloric acid. After extracting the resulting aqueous solution with ethyl acetate, the combined organic layers were then dried over anhydrous magnesium sulfate and filtered. Upon removal of the solvent from the aforesaid filtrate by means of evaporation under reduced pressure, there was obtained a crude residue which was subsequently taken up in methanol and treated with dry hydrogen chloride gas. Evaporation of this mixture in the usual manner, followed by trituration of the residue with dry diethyl ether then gave 0.78 g. of crude product. Recrystallization of the latter material from ethanol/diethyl ether then yielded 0.635 g. (23%) of pure 1'-methyl-1',2',3',4'-tetrahydro-spiro-[imidazolidine-4,4'-quinoline]-2,5-dione hydrochloride, m.p. 247°–249° C. (decomp.). Anal. Calcd. for $C_{12}H_{13}N_3O_2 \cdot HCl$: C, 53.83; H, 5.27; N, 15.70. Found: C, 53.77; H, 5.13; N, 15.88.

EXAMPLE 2

The procedure described in Example 1 was repeated except that 230 mg. (0.00142 mole) of 2,3-dihydro-4(1H)-pyrido(2,3-b)pyridone [prepared according to the procedure described in the *Journal of Medicinal Chemistry*, Vol. 18, p. 1038 (1975)] was the starting material employed in place of 2,3-dihydro-1-methyl-4(1H)-quinolone, using the same molar proportions as before. In this particular case, the corresponding final product obtained was 1'-methyl-1',2',3',4'-tetrahydro-spiro-[imidazolidine-4,4'-pyrido(2,3-b)pyridine]-2,5-dione, m.p. 233°–235° C. after being chromatographed on a silica gel column using ethyl acetate/methanol as the eluant. The yield of pure product amounted to 53 mg. (14%). Anal. Calcd for $C_{11}H_{12}N_4O_2 \cdot 1.75 H_2O$: C, 44.62; H, 4.69; N, 18.92. Found: C, 44.41; H, 4.06; N, 19.05.

EXAMPLE 3

A mixture consisting of 0.47 g. (0.0026 mole) of 7-chloro-2,3-dihydro-4(1H)-quinolone [prepared according to the procedure described in the *Journal of Organic Chemistry*, Vol. 28, p. 1135 (1963)], 2.5 g. (0.0385 mole) of potassium cyanide and 8.0 g. (0.0833 mole) of powdered ammonium carbonate in 40 ml. of 50% aqueous ethanol was placed in a stainless-steel bomb and heated at 80°–85° C. for a period of 48 hours and then at 120° C. for a period of five hours. After cooling to room temperature (~25° C.), the contents of the bomb were diluted with water and then acidified with 6 N hydrochloric acid, followed by treatment with solid sodium bicarbonate. The basified aqueous mixture was next extracted with five-150 ml. portions of ethyl acetate and the combined organic layers were subsequently dried over anhydrous magnesium sulfate and filtered. Upon removal of the solvent from the resulting filtrate by means of evaporation under reduced pressure, there was ultimately obtained a yield of crude product as the residue. Recrystallization of the latter material from methanol-water then gave 0.43 g. (66%) of pure 7'-chloro-1',2',3',4'-tetrahydro-spiro-[imidazolidine-4,4'-quinoline]-2,5-dione, m.p. 278°–280° C. Anal. Calcd. for $C_{11}H_{10}ClN_3O_2$: C, 52.49; H, 4.00; N, 16.70. Found: C, 52.57; H, 3.98; N, 16.74.

EXAMPLE 4

The procedure described in Example 3 was repeated except that 2.0 g. (0.0112 mole) of 6-chloro-2,3-dihydro-4(1H)-quinolone [prepared according to the procedure described in the *Journal of Organic Chemistry*, Vol. 28, p. 1135 (1963)], 1.3 g. (0.02 mole) of potassium cyanide and 4.3 g. (0.0448 mole) of ammonium carbonate were reacted in 40 ml. of 50% aqueous ethanol under the same conditions as before. In this particular case, the corresponding final product obtained was 6'-chloro-1',2',3',4'-tetrahydro-spiro-[imidazolidine-4,4'-quinoline]-2,5-dione, m.p. 293°–295° C. The yield of pure product was 8% of the theoretical value. Anal. Calcd for $C_{11}H_{10}ClN_3O_2 \cdot \frac{1}{8}H_2O$: C, 52.03; H, 4.07; N, 16.35. Found: C, 51.99; H, 3.80; N, 16.54.

EXAMPLE 5

The following tetrahydroquinoline-derived spirohydantoin compounds are prepared by employing the procedure described in the previous examples, starting from readily available materials in each instance:

1'-(n-butyl)-1',2',3',4'-tetrahydro-spiro-[imidazolidine-4,4'-quinoline]-2,5-dione 6'-fluoro-1',2',3',4'-tetrahydro-spiro-[imidazolidine-4,4'-quinoline]-2,5-dione 7'-bromo-1',2',3',4'-tetrahydro-spiro-[imidazolidine-4,4'-quinoline]-2,5-dione 6',7'-dichloro-1',2',3',4'-tetrahydro-spiro-[imidazolidine-4,4'-quinoline]-2,5-dione 6',8'-dichloro-1',2',3',4'-tetrahydro-spiro-[imidazolidine-4,4'-quinoline]-2,2-dione
1'-methyl-6'-fluoro-1',2',3',4'-spiro-[imidazolidine-4,4'-quinoline]-2,5-dione
1'-ethyl-7'-phenyl-1',2',3',4'-tetrahydro-spiro-[imidazolidine-4,'-quinoline]-2,5-dione
6',7'-diphenyl-1',2',3',4'-tetrahydro-spiro-[imidazolidine-4,4-quinoline]-2,5-dione
5'-methoxy-1',2',3',4'-tetrahydro-spiro-[imidazolidine-4,4'-quinoline-2,5-dione
7'-(n-butoxy)-1',2',3',4'-tetrahydro-spiro-[imidazolidine-4,4'-quinoline]-2,5-dione
6',7'-dimethoxy-1',2',3',4'-tetrahydro-spiro-[imidazolidine-4,4'-quinoline]-2,5-dione
6',7'-di(n-butoxy)-1',2',3',4'-tetrahydro-spiro-[imidazolidine-4,4'-quinoline]-2,5-dione
6',7'-methylenedioxy-1',2',4'-tetrahydro-spiro-[imidazolidine-4,4'-quinoline]-2,5-dione
6',7'-ethylenedioxy-1',2',3',4'-tetrahydro-spiro-[imidazolidine-4,4'-quinoline]-2,5-dione
1',2',3',4'-tetrahydro-spiro-[imidazolidine-4,4'-pyrido(2,3-b)pyridine]-2,5-dione
1'-ethyl-1',2',3',4'-tetrahydro-spiro-[imidazolidine-4,4'-pyrido(2,3-b)pyridine]-2,5-dione
1'-isopropyl-1',2',3',4'-tetrahydro-spiro-[imidazolidine-4,4'-pyrido(2,3-b)pyridine]-2,5-dione
1'-(n-butyl)-1',2',3',4-tetrahydro-spiro-[imidazolidine-4,4'-pyrido(2,3-b)pyridine]-2,5-dione.

EXAMPLE 6

The non-toxic hydrohalide acid addition salts of each of the previously reported tetrahydroquinoline-derived spiro-hydantoin base compounds of this invention, such as the corresponding novel hydrochloride, hydrobromide and hydroiodide salts, are each individually prepared by first dissolving the respective organic base compound in absolute ether followed by the introduction of the appropriate hydrohalide gas into the reaction solution until saturation of same is complete with respect to said gas, whereupon the desired acid addition salt soon precipitates from said solution. In this way, 1.0 g. of 7'-chloro-1',2',3',4'-tetrahydro-spiro-[imidazolidine-4,4'-quinoline]-2,5-dione, obtained as a free base product in Example 3, is converted via dry hydrogen bromide gas to the corresponding hydrobromide acid addition salt in substantially quantitative yield.

EXAMPLE 7

The nitrate, sulfate or bisulfate, phosphate or acid phosphate, acetate, lactate, maleate, fumarate, citrate or acid citrate, tartrate or bitartrate, succinate, gluconate, saccharate, methanesulfonate, ethanesulfonate, benzenesulfonate and p-toluenesulfonate salts of each of the aforementioned tetrahydroquinoline-derived spiro-hydantoin base compounds reported previously are each prepared by dissolving the proper molar amounts of the respective acid and base in separate portions of ethanol and then mixing the two solutions together, followed by the addition of diethyl ether to the resultant mixture in order to effect precipitation of the desired acid addition salt therefrom. In this manner, equimolar amounts of 7'-chloro-1',2°,3',4-tetrahydro-[imidazolidine-4,4'-quinoline]-2,5-dione and concentrated sulfuric acid react to afford the corresponding sulfuric acid addition salt. In like manner, each of the other salts is prepared.

EXAMPLE 8

A dry solid pharmaceutical composition is prepared by blending the following materials together in the proportions by weight specified below:

| | |
|---|---|
| 7'-chloro-1',2',3',4'-tetrahydro-spiro-[imidazolidine-4,4'-quinoline]-2,5-dione | 50 |
| Sodium citrate | 25 |
| Alginic acid | 10 |
| Polyvinylpyrrolidone | 10 |
| Magnesium stearate | 5 |

After the dried compound is thoroughly blended, tablets are punched from the resulting mixture, each tablet being of such size that it contains 200 mg. of the active ingredient. Other tablets are also prepared in a similar fashion containing 25, 50 and 100 mg. of the action ingredient, respectively, by merely using the appropriate amount of the hydantoin compound in each case.

EXAMPLE 9

A dry solid pharmaceutical composition is prepared by combining the following materials together in the proportions by weight indicated below:

| | |
|---|---|
| 7'-Chloro-1',2',3',4'-tetrahydro-spiro-[imidazolidine-4,4'-quinoline]-2,5-dione | 50 |
| Calcium carbonate | 20 |
| Polyethylene glycol, average molecular weight 4000 | 30 |

The dried solid mixture so prepared is then thoroughly agitated so as to obtain a powdered product that is completely uniform in every respect. Soft elastic and hard-filled gelatin capsules containing this pharmaceutical composition are then prepared, employing a sufficient quantity of material in each instance so as to provide each capsule with 250 mg. of the active ingredient.

EXAMPLE 10

The following tetrahydroquinoline-derived spiro-hydantoin compounds of Examples 1–4, respectively, were tested for their ability to reduce or inhibit aldose reductase enzyme activity via the procedure of S. Hayman et al., as described in the *Journal of Biological Chemistry*, Vol. 240, p. 877 (1965) and as modified by K. Sestanj et al. in U.S. Pat. No. 3,821,383. In every case, the substrate employed was partially purified aldose reductase enzyme obtained from calf lens. The results obtained with each compound are expressed below in terms of their ability to achieve a 50% reduction (i.e., inhibition) in aldose reductase enzyme activity with respect to the particular concentration level indicated (the latter value actually represents the so-called $IC_{50}$ value):

| Compound | Concentration Level ($IC_{50}$) |
|---|---|
| Product of Example 1 | $5 \times 10^{-5}$M |
| Product of Example 2 | $1 \times 10^{-5}$M |
| Product of Example 3 | $1 \times 10^{-5}$M |
| Product of Example 4 | $1 \times 10^{-6}$M |

EXAMPLE 11

The following tetrahydroquinoline-derived spiro-hydantoin compounds of Examples 1 and 3-4, respectively, were tested for their ability to reduce or inhibit sorbitol accumulation in the sciatic nerve of streptozotocinized (i.e., diabetic) rats by the procedure essentially described in U.S. Pat. No. 3,821,383. In the present study, the amount of sorbitol accumulation in the sciatic nerves was measured 27 hours after induction of diabetes. The compounds were administered orally at the dose levels indicated at 4, 8 and 24 hours following the administration of streptozotocin. The results obtained in this manner are presented below in terms of percent inhibition (%) afforded by the test compound as compared to the case where no compound was administered (i.e., the untreated animal where sorbitol levels normally rise from approximately 50-100 mM/g. tissue to as high as 400 mM/g. tissue in the 27-hour test period):

| Compound | Percent Inhibition (%) | |
|---|---|---|
| | 5.0 mg/kg | 10 mg/kg |
| Product of Example 1 | 19 | — |
| Product of Example 3 | 23 | — |
| Product of Example 4 | — | 80 |

I claim:

1. A compound selected from the group consisting of tetrahydroquinoline-derived spiro-hydantoin bases of the formula

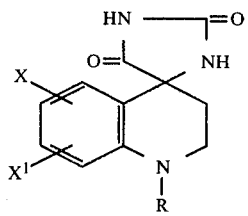

and the pharmaceutically acceptable acid addition salts thereof, wherein

X is hydrogen and $X^1$ is lower alkoxy, fluorine, chlorine, bromine or phenyl; or X and $X^1$, when taken separately, are each lower alkoxy, chlorine or phenyl, and when taken together are $-OCH_2(CH_2)_nO-$ wherein n is zero or one; and R is hydrogen or lower alkyl.

2. A compound as claimed in claim 1 of the formula I wherein X is hydrogen and $X^1$ is chlorine and R is hydrogen.

3. A compound as claimed in claim 2 wherein $X^1$ is chlorine at the 6-position of the molecule.

4. A compound as claimed in claim 2 wherein $X^1$ is chlorine at the 7-position of the molecule.

5. 6'-Chloro-1',2',3+,4'-tetrahydro-spiro-[imidazolidine-4,4'-quinoline]-2,5-dione.

6. 7'-Chloro-1',2',3',4'-tetrahydro-spiro-[imidazolidine-4,4'-quinoline]-2,5-dione.

7. A method for treating a diabetic host to prevent or alleviate ocular or neuritic diabetes-associated chronic complications, which comprises administering to said diabetic host an alleviating or prophylactically effective amount of a compound as claimed in claim 1.

8. A composition suitable for oral administration comprisng a pharmaceutically acceptable carrier and a compound as claimed in claim 1 in an amount effective for the treatment of ocular or neuritic diabetes-associated chronic complications.

* * * * *